Figure 1:
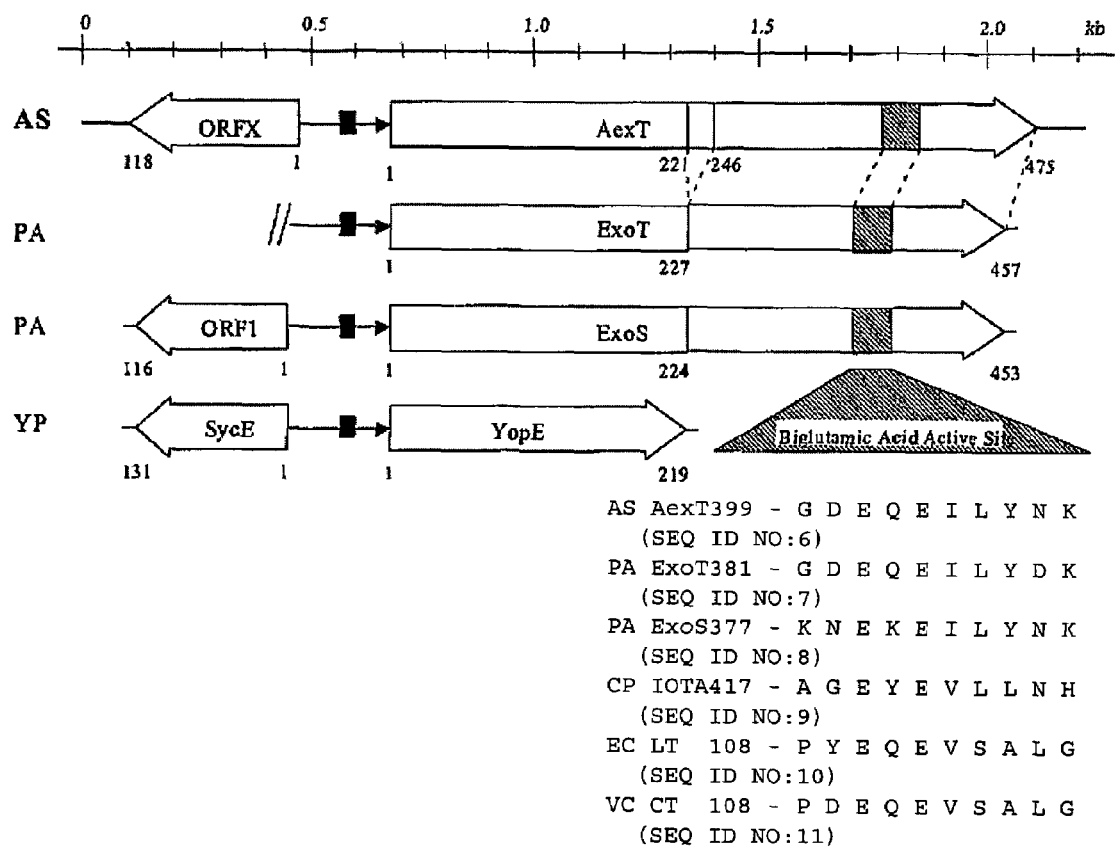

US007351550B2

(12) United States Patent
Frey et al.

(10) Patent No.: US 7,351,550 B2
(45) Date of Patent: Apr. 1, 2008

(54) **EXOENZYME TOXIN OF *AEROMONAS SALMONICIDA*, AND USES THEREOF**

(75) Inventors: Joachim Frey, Bern (CH); Peter Kuhnert, Baetterkinden (CH); Julian C. Thornton, deceased, late of Victoria (CA); by Tracy A. Thornton, legal representative, Victoria (CA); Michael A. Kuzyk, Richmond (CA); Jan Burian, Victoria (CA); Martin Braun, Zug (CH)

(73) Assignee: Universitat Bern, Bern (CH)

( * ) Notice: Subject to any disclaimer, the term of this patent is extended or adjusted under 35 U.S.C. 154(b) by 253 days.

(21) Appl. No.: 10/416,981

(22) PCT Filed: Nov. 15, 2001

(86) PCT No.: PCT/CA01/01600

§ 371 (c)(1),
(2), (4) Date: Oct. 5, 2004

(87) PCT Pub. No.: WO02/40515

PCT Pub. Date: May 23, 2002

(65) Prior Publication Data

US 2005/0158344 A1 Jul. 21, 2005

Related U.S. Application Data

(60) Provisional application No. 60/248,864, filed on Nov. 15, 2000.

(51) Int. Cl.
*C12P 21/06* (2006.01)

(52) U.S. Cl. .................. 435/69.1; 536/23.7; 536/24.1; 536/24.2; 435/69.3; 435/71.1; 435/243; 435/252.1; 435/252.3; 435/320.1; 424/236.1; 424/234.1

(58) Field of Classification Search ............... 536/23.7, 536/24.1, 24.2; 435/69.1, 69.3, 71.1, 243, 435/252.1, 252.3, 320.1; 424/236.1, 234.1
See application file for complete search history.

(56) References Cited

FOREIGN PATENT DOCUMENTS

| | | |
|---|---|---|
| WO | WO 92/21370 | 12/1992 |
| WO | WO 97/23503 | 7/1997 |

OTHER PUBLICATIONS

Bowie et al., Science 247:1306-1310, p. 1306.*
Mikayama et al. (Nov. 1993. Proc.Natl.Acad.Sci. USA, vol. 90 : 10056-10060).*
Rudinger et al. (Jun. 1976. Peptide Hormones. Biol.Council. pp. 5-7).*
Braun et al. (Submitted. Jul. 19, 2000. GenEmbl: Database. Accession No. AF288366).*
Database Swall 'Online! EBI; Nov. 1, 1996 "ExoT of *P. aeruginosa*," Database Accession No. Q51445, XP-002216069.
Database EMBL 'Online! EBI; Aug. 2, 2001 "*Aeromonas salmonicida* ADP-ribosyltransferase gene (aexT), complete cds and unknown gene," Database Accession No. AF288366, XP-002216070.
Database Swall 'Online! EBI; Nov. 1, 1996 "ExoS of *P. aeruginosa*" Database Accession No. Q51448, XP-002216071.

* cited by examiner

*Primary Examiner*—Jennifer E. Graser
(74) *Attorney, Agent, or Firm*—Womble Carlyle Sandridge & Rice, PLLC

(57) ABSTRACT

A protein toxin named *Aeromonas salmonicida* exoenzyme T (AexT), which belongs to the family of ADP-ribosylating toxins, is disclosed as is a Calcium (or other cation concentration) dependent promoter of *A. salmonicida*. Also disclosed are diagnostic, preventive, and therapeutic techniques, including the preparation of bacterin vaccines based on AexT for inducing immunity against *A. salmonicida* infections.

11 Claims, 3 Drawing Sheets

EXOENZYME TOXIN OF *AEROMONAS SALMONICIDA*, AND USES THEREOF

CROSS REFERENCE TO RELATED APPLICATION

This claims the benefit of U.S. Provisional Application No. 60/248,864, filed Nov. 15, 2000.

FIELD OF THE INVENTION

This invention relates to bacterial toxins and to bacterial promoters, and in particular to a newly identified and characterized toxin and promoter of *Aeromonas salmonicida*. The invention also encompasses methods for the production or accumulation of the *A. salmonicida* toxin, as well as the diagnostic, therapeutic, and preventative use (including in particular the preparation of traditional or recombinant protein or DNA vaccines) of the *A. salmonicida* toxin. Also encompassed are methods for improving *A. salmonicida* bacterin vaccines by controlling expression of the toxin.

BACKGROUND OF THE INVENTION

The fish disease furunculosis derived its name from the characteristic lesions observed as furuncles formed on the surface of fish as a result of infection with *Aeromonas salmonicida*. This pathogen causes most severe losses in production farms of salmon and trout, and leads to the use of large amounts of antibiotics in closed and open waters for therapy of fununculosis. In order to develop efficient strategies to prevent *A. salmonicida* outbreaks, it is essential to know the main mechanisms of pathogenicity of *A. salmonicida*.

Several potential virulence factors of *A. salmonicida* have been described thus far. They include the surface array-layer protein, the hemolysins ASH1, ASH3, ASH4, H-lysin, salmolysin, the serine protease AspA and the Glycerophospholipid:Cholesterol Acyltransferase (GCAT) complexed with lipopolysaccharide (LPS). While there are many reports on potential virulence factors of *A. salmonicida*, in particular hemolysins, little is known about their activity and their role in pathogenesis. Many of them seem not to play a primary role in pathogenesis, since deletion mutants of GCAT and aspA genes showed neither of them to be essential for acute *A. salmonicida*-induced furunculosis. AspA however is essential for pro-GCAT processing in broth cultures and might also be involved in activation of other secreted enzymes or toxins.

Various attempts have been made to develop vaccines to prevent *A. salmonicida* infections mainly on the basis of killed cells (bacterins). Current vaccines achieve some level of protection. However, the nature of the antigens in efficient vaccines is not well defined. Significant differences of protein patterns are seen in cultures of *A. salmonicida* grown in vivo by an intraperitoneal implant technique in rainbow trout compared to cultures grown in vitro in culture medium. Such differences are thought to be the reasons of variable efficacy of former furunculosis vaccines due to a lack of appropriate antigens in certain vaccine preparations.

Several pathogenic bacteria use ADP-ribosylation as a key mechanism to modify properties of host cell proteins, thus to modulate their function and induce disease. Hence ADP-ribosylation of eukaryotic regulatory proteins is the underlying pathogenic mechanism of a heterogeneous family of bacterial protein toxins. ADP-ribosylating toxins are broadly distributed among highly pathogenic bacteria and are the primary cause of various severe human diseases such as diphtheria, cholera and pertussis. Among them, the ADP-ribosyltransferase toxin called exoenzyme S (ExoS) of *Pseudomonas aeruginosa* is one of the most prominent representatives. It is secreted via a type III-dependent secretion mechanism. Type II secretion systems generally have the potential to recognize receptors on target cells, induce biosynthesis of the corresponding toxins, and finally inject these bacterial toxins directly into the host cells without secretion to the medium. Recently, it was shown that ExoS is a bifunctional toxin containing an N-terminal part resembling the *Yersiniae* YopE toxin which catalyses rho-dependent actin depolymerisation, and a C-terminal ADP-ribosylating domain. Unique to most bacterial toxins, the ADP-ribosylating toxin ExoS does not have a rigid target protein specificity and ribosylates a number of target proteins including IgG3, apolipoprotein A-I, vimentin and several members of the Ras superfamily. Intracellular expression of the amino-terminal domain of ExoS elicits the disruption of actin, while expression of the carboxyl-terminal domain of ExoS possesses FAS (factor activating exoenzyme S)-dependent ADP-ribosyltransferase activity and is cytotoxic to eukaryotic cells. FAS is a member of the 14-3-3 family of proteins that regulate the activity of several eukaryotic enzymes. Prior to this invention, no analogues to ExoS have been found in bacteria other than *P. aeruginosa*.

SUMMARY OF THE INVENTION

A protein toxin named *Aeromonas salmonicida* exoenzyme T (AexT), which belongs to the family of ADP-ribosylating toxins, was identified and characterized in *Aeromonas salmonicida*, the etiological agent of furunculosis in fish. This discovery has enabled the development of diagnostic, preventative, and therapeutic techniques, including the preparation of traditional or recombinant vaccines based on AexT for inducing immunity against *A. salmonicida* infections, and including the identification and characterization by known methods of homologous toxins and promoters in other *Aeromonas* species or other bacterial genera. Also identified and characterized was the Calcium- (or other cation concentration-) dependent promoter of *A. salmonicida*. This novel promoter is useful for regulating the expression of proteins in recombinant expression systems.

In one embodiment, the invention comprises an isolated nucleic acid segment (SEQ ID NO:1) encoding a 50 kDa exoenzyme of *A. salmonicida*. In another embodiment, the invention comprises a nucleic acid segment that encodes a protein having the amino acid sequence of SEQ ID NO:2, including variants that retain either biological activity or immunogenicity or both. Due to the degeneracy of the genetic code and the possible presence of flanking nucleic acid fragments outside of the coding region, it will be understood that many different nucleic acid sequences may encode the amino acid sequence of SEQ ID NO:2 and variants, and that all such sequences would be encompassed within the present invention.

In a further embodiment, a method of producing, protecting, capturing, or preserving AexT toxin by growing *A. salmonicida* on $Ca^{2+}$ or other cations depleted medium is provided. This provides a means of preparing a vaccine that is much more effective than currently available vaccines against *A. salmonicida*. In another embodiment, the invention relates to the use of AexT as an immunogen and to the use of AexT in a recombinant or traditional vaccine to reduce the incidence of infection by *A. salmonicida*.

In another embodiment, the invention comprises an improved bacterin vaccine in which the production of AexT has been induced prior to inactivation of the A. salmonicida cells, or in which A. salmonicida has been manipulated (using recombinant or other means) to constitutively express AexT prior to inactivation.

In a further embodiment, the invention provides a means of diagnosing A. salmonicida, or other bacteria found to contain AexT homologues, by the detection of the AexT protein or the homologous proteins. Also, the invention provides a toxin that in itself may have therapeutic activity in certain unrelated disease states, or for treatment of certain conditions in man or animals.

In a further embodiment, the invention comprises an isolated nucleic acid segment (SEQ ID NO:3) encoding the promoter sequence of the gene encoding the AexT protein. This promoter is regulated by Calcium, and possibly by other cations as well as other undefined sensory signals, and is useful for regulating the expression of proteins in recombinant expression systems.

The gene aexT encoding the toxin AexT, was identified by broad range toxin gene probes. It was cloned and characterized by sequence analysis. The cloned gene was expressed, and purified AexT was obtained by recombinant gene technology in E. coli. AexT shows significant sequence similarity to the ExoS and ExoT exotoxins of Pseudomonas aeruginosa and to the YopE cytotoxin of Yersiniae sp. Recombinant AexT possesses enzymatic ADP-ribosyltransferase activity. Monospecific polyclonal antibodies directed against purified recombinant AexT cross-react with ExoS and ExoT of P. aeruginosa. Secretion of AexT from freshly isolated strains of A. salmonicida requires medium depleted of free $Ca^{2+}$ ions (or other cations) or necessitates contact with fish cells, as demonstrated with cultivated rainbow trout gonad cells. These cells undergo significant morphological changes upon infection through the toxic activity of AexT. The dependence on fish cells or on $Ca^{2+}$ (or other cation) restricted conditions for the expression and secretion of the AexT protein toxin by A. salmonicida indicates that regulation of expression of the aexT gene and secretion of AexT is coupled to a type III secretion system.

The induction of AexT biosynthesis in A. salmonicida is regulated through contact with target cells via a sensory process similar to that found in Yersiniae sp. as indicated by the orfX gene flanking the aexT gene. The orfX shows high similarity to the gene for specific Yop chaperon E (sycE) of Yersiniae. SycE serves as a secretion signal and is part of the type III secretion pathway for secretion of YopE. Cultures of the A. salmonicida type strain ATCC $33658^T$, which were passaged in vitro for a large number of generations, and which seem to have lost virulence, do not produce significant amounts of AexT and do not affect rainbow trout gonad cells morphologically upon infection in spite of the presence of the aexT gene, in contrast to a fresh field isolate of A. salmonicida. The ADP-ribosylating toxin AexT is a determinative virulence factor of A. salmonicida and is expected to provide new insights in basic mechanisms of virulence of this pathogen, and potentially a protective antigen for vaccination against furunculosis.

Sequence Listing

The nucleic and amino acid sequences listed in the accompanying sequence listing are shown using standard letter abbreviations for nucleotide bases, and one letter code for amino acids. Only one strand of each nucleotide acid sequence is shown, but the complementary strand is understood as included by any reference to the displayed strand.

Aeromonas salmonicida gene for aexT complete coding DNA sequence.

| | | | | | |
|---|---|---|---|---|---|
| ATGCAGA | TTCAAGCAAA | CACCGTCGGC | | | Seq ID 1 |
| ACACAGGCCG | TCGCTCACCA | CAGTGATGCC | ACGACCGGAG | TTGGCCGGAT | |
| GGGTCAGATG | GAGGCGCGTC | AGGTCGCCAC | CGGACAAGAT | GCGATCCTGC | |
| TGGGCAGTCG | CAGCGAACCG | CAAAAAGGGC | AGGGGCTGCT | CTCGCGACTG | |
| GGGGCCCAGC | TGGCCCGCCC | GTTCGTGGCC | ATCAAAGAGT | GGATCAGCAA | |
| CCTGCTGGGG | ACGGACAAGC | GTGCCGCTGC | GCCGAAGGCG | CAAACCGCCG | |
| TTTCCCCCGA | GGATCTTCAG | CGACTGATGA | AGCAGGCTGC | ATTTGGTAGC | |
| TCGCTGGGTG | GCTTCGCCAA | GGCGGACGTG | TTGAACAACA | TCACAGGCGA | |
| ACAATTGGGC | AAGGATCACG | CCAGTCTGGC | GACCGGCAAT | GGCCCCCTGC | |
| GCTCTCTCTG | CACCGCGTTG | CAGGCCGTTG | TCATAGGATC | TCAGCAACCG | |
| CAACTCCGGG | AGTTGGCTAC | CGGGCTGCTG | GCCCGCCCCA | TCGCCGGTAT | |
| CCCGCTCCAG | CAGTGGGGGT | CGGTAGGCGG | CAAGGTGACC | GAGCTGCTCA | |
| CCAGCGCCCC | CCCCGAACTG | TTGAAGGAGG | CTATGAGCCA | GCTACACACC | |
| GCGATGGGTG | AAGTTGCCGA | CCTGCAGCGC | GCTGTAAAGG | CAGAAGTTGC | |
| TGGCGAACCG | GCGCGAAGCG | CGACCACAGC | GGCCGCTGTG | GCGCCGCTCC | |
| AAAGCGGTGA | GAGCGAAGTT | AACGTTGAGC | CTGCCGACAA | GGCGCTGGCA | |

-continued

| *Aeromonas salmonicida* gene for aexT complete coding DNA sequence. |
| --- |
| GAGGGCTTGC AGGAGCAATT CGGCCTGGAG GCCGAGCAAT ATCTGGGTGA |
| ACAGCCCCAC GGTACTTACA GCGATGCTGA AGTGATGGCG CTTGGGCTCT |
| ACACCAACGG CGAATACCAG CACCTGAATC GCTCGCTGCG TCAGGAAAAG |
| CAGCTGGATG CAGGGCAAGC GTTGATCGAT CAGGGTATGT CCACCGCTTT |
| TGAGAAAAGT ACCCCCACCG AGCAGTTGAT CAAGACCTTC CGCGGTACCC |
| ACGGCGGCGA TGCGTTCAAC GAGGTGGCAG AGGGGCAAGT CGGTCATGAT |
| GTCGCTTATC TTTCCACCTC TCGGGATCCC AAGGTGGCAA CCAACTTTGG |
| TGGTTCAGGC TCCATATCCA CGATATTTGG CCGCTCGGGG ATCGATGTCA |
| GCGACATATC CGTTGAAGGT GACGAGCAGG AGATCCTCTA TAACAAAGAG |
| ACTGATATGC GGGTATTGCT CAGTGCCAAA GATGAACGGG GCGTCACCCG |
| GCGGGTACTG GAAGAGGCCT CGCTGGGGGA ACAAAGCGGC CACAGCAAGG |
| GGCTGCTGGA CGGGCTGGAT CTGGCAAGAG GAGCGGGCGG TGCCGACAAG |
| CCGCAAGAGC AAGATATCCG TCTGAAGATG CGCGGGCTCG ATTTGGCGTG |
| A |

| *Aeromonas salmonicida* protein sequence for the AexT protein | |
| --- | --- |
| 1 MQIQANTVGT QAVAHHSDAT TGVGRMGQME ARQVATGQDA ILLGSRSEPQ | Seq ID 2 |
| 51 KGQGLLSRLG AQLARPFVAI KEWISNLLGT DKRAAAPKAQ TAVSPEDLQR | |
| 101 LMKQAAFGSS LGGFAKADVL NNITGEQLGK DHASLATGNG PLRSLCTALQ | |
| 151 AVVIGSQQPQ LRELATGLLA RPIAGIPLQQ WGSVGGKVTE LLTSAPPELL | |
| 201 KEAMSQLHTA MGEVADLQRA VKAEVAGEPA RSATTAAAVA PLQSGESEVN | |
| 251 VEPADKALAE GLQEQFGLEA EQYLGEQPHG TYSDAEVMAL GLYTNGEYQH | |
| 301 LNRSLRQEKQ LDAGQALIDQ GMSTAFEKST PTEQLIKTFR GTHGGDAFNE | |
| 351 VAEGQVGHDV AYLSTSRDPK VATNFGGSGS ISTIFGRSGI DVSDISVEGD | |
| 401 EQEILYNKET DMRVLLSAKD ERGVTRRVLE EASLGEQSGH SKGLLDGLDL | |
| 451 ARGAGGADKP QEQDIRLKMR GLDLA* | |

| *Aeromonas salmonicida* promoter sequence for the AexT gene | |
| --- | --- |
| TGATG GCTCCAGATT GATGATGGCG | Seq ID 3 |
| CCATTAGAGC AGGTCGCCGC CAGCGGCACT GTTAATGGTG GCTCTCATTT | |
| TTTAGCTTTT CGGTCAGCAG GATGGCGCGC CGCGCTCAGT ACAAAAATCG | |
| CGACCAATCC CGATAGTCCC TGTTGATACC CTCTCCTAGA CTGGCGGCGA | |
| AACATCACAA GAAGACAATC ATC | |

| *Aeromonas salmonicida* protein sequence for the OrfX protein | | | | | |
|---|---|---|---|---|---|
| 1MNSLYHAAIH | QLFLSLSLPQ | PQQEESVTSL | QIGELTCHLT | EHPADYLLMF | Seq ID 4 |
| 51TRLEVASGAQ | AAAQNLFSQD | PCKPVLGFDP | DDLTPVLWSR | QPLQQLDRAQ | |
| 101IHHQVEQLVS | AADELSRW* | | | | |

| *Aeromonas salmonicida* gene for orfX complete coding DNA sequence | | | | | |
|---|---|---|---|---|---|
| TT ACCACCTGCT TAGCTCGTCA GCGGCAGAGA | | | | | Seq ID 5 |
| CCAGTTGCTC | CAGCTGGTGA | TGGATCTGGG | CGCGATCCAG | CTGCTGCAAC | |
| GGCTGGCGAC | TCCACAACAC | CGGCGTCAGA | TCGTCGGGGT | CAAAACCCAG | |
| AACGGGTTTG | CAAGGGTCCT | GACTAAACAG | GTTTTGCGCG | GCGGCCTGGG | |
| CGCCGCTAGC | TACCTCAAGA | CGGGTAAACA | TCAGCAGATA | GTCGGCTGGG | |
| TGCTCGGTCA | GGTGGCAGGT | CAGTTCGCCG | ATCTGCAGGC | TGGTGACGCT | |
| TTCCTCCTGC | TGCGGCTGAG | GAAGCGAGAG | GGAGAGAAAC | AGCTGGTGGA | |
| TGGCGGCGTG | ATAAAGAGAG | TTCAT | | | |

BRIEF DESCRIPTION OF THE DRAWINGS

FIG. 1. Genetic map of the genes encoding AexT and the ORFX of *A. salmonicida* in alignment with the corresponding genes of *P. aeruginosa* and *Y. pestis*. Maps were constructed from EMBL/GenBank Accession no L27629 for *P. aeruginosa* ExoS, L46800 for *P. aeruginosa* ExoT and from AF053946 for *Y. pestis*. Due to the high homology found within the virulence plasmids of *Y. pestis, Y. pseudotuberculosis* and *Y. enterecolitica*, AF053946 also represents these *Yersiniae* sp. Boxes with arrowheads indicate ORFs. Numbers indicate corresponding amino acid positions. The putative biglutamic acid active site is dashed and the alignment with other ADP-ribosylating toxins is shown at the bottom. Black boxes indicate the transcription activator (ExsA) binding site and black triangles indicate consensus sequences for the transcription promoter, containing −10 and −35-boxes. Abbreviations used: AS, *A. salmonicida*; PA, *P. aeruginosa*; YP, *Y. pestis*; CP, *Clostridium perfringens*; EC, *E. coli*; VC, *V. cholera*; AexT, *Aeromonas exoenzyme* T; ExoS, exoenzyme S; ExoT, exoenzyme T; SycE, specific Yop chaperone E; YopE, *Yersinia* outer protein E; IOTA, IOTA toxin; LT, heat labile toxin; CT, cholera toxin. Scale on top is given in kb.

FIG. 2. Immunoblot reacted with rabbit serum raised against nitrilotriacetic acid-purified recombinant AexT-His (Lane 5). Equal amounts of supernatants derived from *A. salmonicida* strains were mixed with SDS-loading buffer and loaded onto a 10% SDS-polyacrylamide gel. *A. salmonicida* strains JF2267 (Lane 1 and 3) and ATCC 33658 (Lane 2 and 4) were grown in standard media (Lane 1 and 2) or in Calcium depleted media containing 10 mM NTA (Lane 3 and 4). The molecular masses of the prestained broad range protein markers (BioLabs, Std.) are indicated in kDa to the left.

FIG. 3. Infection of fish cells with *A. salmonicida*. RTG-2 cells were exposed to 100 μl PBS containing no cells (A), *A. salmonicida* ATCC 33658 (B) and *A. salmonicida* JF2267 (C). Bacteria in panel C seem to be attached to cells and cell debris whereas bacteria in panel B are equally distributed over the whole surface and were observed to be floating in the medium. Pictures were taken after 24 hrs of infection under a phase contrast microscope.

DETAILED DESCRIPTION OF THE INVENTION

I. Definitions:

Epitope: An epitope refers to an immunologically active region of an immunogen (most often a protein, but sometimes also a polysaccharide or lipid or other molecule) that binds to specific membrane receptors for antigen on lymphocytes or to secreted antibodies. To generate an immune response to a foreign antigen, lymphocytes and antibodies recognize these specific regions (epitopes) of the antigen rather than the entire molecule.

B cell epitope: The region of an immunogen which is recognized by B cells when it binds to their membrane bound antibody. The B cells which recognize that particular region then proliferate and secrete antibody molecules which are specific for that region of the immunogen. B cell epitopes tend to be highly accessible regions on the exposed surface of the immunogen. Stimulation of the immune system by B cell epitopes results in "humoral" immunity.

T cell epitope: The region (epitope) of an immunogen which is recognized by a receptor on T cells after being processed and presented on the surface of an antigen presenting cell (APC) in the context of a major histocompatability complex (MHC) class I or II molecule. T cells can be split into two distinct groups, T helper cells ($T_h$) and T cytotoxic cells ($T_c$). T helper cells recognize epitopes bound to MHC class II molecules whereas T cytotoxic cells recognize epitopes bound to MHC class I molecules. T helper cells can be further subdivided into two classes, $T_{h1}$ and $T_{h2}$, $T_{h1}$ being responsible for stimulation of cell-mediated immunity and $T_{h2}$ cells stimulating the humoral arm of the immune system. When a given T cell recognizes the epitope-MHC complex at the surface of the APC it becomes stimulated and proliferates, leading to the production of a large number of T cells with receptors specific for the stimulating epitope. Stimulation of the immune system by T cell epitopes normally results in "cell-mediated" immunity.

Attenuated Bacterial Vaccine: This refers to bacterial strains which have lost their pathogenicity while retaining their capacity for transient growth within an inoculated host. Because of their capacity for transient growth, such vaccines provide prolonged immune-system exposure to the individual epitopes on the attenuated organisms, resulting in increased immunogenicity and memory-cell production, which sometimes eliminates the need for repeated booster injections. The ability of many attenuated vaccines to replicate within host cells makes them very suitable to induce a cell-mediated immunity. Typically, bacterial strains are made attenuated by introducing multiple defined gene mutations into the chromosome thereby impairing growth in vivo.

Recombinant Vector Vaccine: This refers to the introduction of genes (or pieces of genes) encoding major antigens (or epitopes) from especially virulent pathogens into attenuated viruses or bacteria. The attenuated organism serves as a vector, replicating within the host and expressing the gene product of the pathogen.

Traditional Vaccine: A traditional vaccine is a preparation yielding protection from disease based on: an inactivated whole pathogen; an attenuated live pathogen; a closely related organism (live or dead) sharing protective epitopes; a toxin; a chemically modified or heated toxin; or a purified or partially purified protein from the pathogen or a closely related organism.

Sequence Identity: Identity between two nucleic acid sequences, or two amino acid sequences is expressed in terms of the level of identical residues shared between the sequences. Sequence identity is typically expressed in terms of percentage identity; the higher the percentage, the more similar the two sequences are.

Sequence Similarity: Similarity between two amino acid sequences is expressed in terms of the level of sequence conservation, including shared identical residues and those residues which differ but which share a similar size, polarity, charge or hydrophobicity. Sequence similarity is typically expressed in terms of percentage similarity; the higher the percentage, the more similar the two sequences are.

Recombinant: A recombinant nucleic acid is one that has a sequence that is not normally occurring or has a sequence that is made by an artificial combination of two otherwise separated segments of sequence. This artificial combination is often accomplished by chemical synthesis or, more commonly, by the artificial manipulation of isolated segments of nucleic acids, e.g., by genetic engineering techniques.

Oligonucleotide (oligo): A linear polymer sequence of up to approximately 100 nucleotide bases in length.

Probes and primers: Nucleic acid probes and primers may readily be prepared based on the amino acid and DNA sequence provided by this invention. A probe comprises an isolated nucleic acid attached to a detectable label or reporter molecule. Typical labels include radioactive isotopes, ligands, chemiluminescent agents, and enzymes. Methods for labelling and guidance in the choice of labels appropriate for various purposes are well known in the art.

Primers are short nucleic acids, preferably DNA oligonucleotides 15 nucleotides or more in length. Primers may be annealed to a complementary target DNA strand, and then extended along the target DNA strand by a DNA polymerase enzyme. Primer pairs can be used for amplification of a nucleic acid sequence, e.g., by the polymerase chain reaction (PCR) or other nucleic-acid amplification methods known in the art.

Methods for preparing and using probes and primers are well known in the art. PCR primer pairs can be derived from a known sequence, for example, by using computer programs intended for that purpose such as DNAStar Lasergene software. One of skill in the art will appreciate that the specificity of a particular probe or primer increases with its length. Thus, for example, a primer comprising 20 consecutive nucleotides will anneal to a target with a higher specificity than a corresponding primer of only 15 nucleotides. Thus, in order to obtain greater specificity, probes and primers may be selected that comprise 20, 25, 30, 35, 40, 50 or more consecutive nucleotides.

Isolated: An "isolated" biological component (such as nucleic acid or protein or organelle) has been substantially separated or purified away from other biological components in the cell of the organism in which the component naturally occurs, i.e., other chromosomal and extra-chromosomal DNA and RNA, proteins and organelles. Nucleic acids and proteins that have been "isolated" include nucleic acids and proteins purified by standard purification methods. The term also embraces nucleic acids and proteins prepared by recombinant expression in a host cell as well as chemically synthesized nucleic acids. An "isolated" bacterial strain or colony is purified away from other colonies and yields a pure culture without any contaminants upon plating on selective media.

Vector: A nucleic acid molecule as introduced into a host cell, thereby producing a transformed host cell. A vector may include nucleic acid sequences that permit it to replicate in a host cell, such as an origin of replication. A vector may also include one or more selectable marker genes and other genetic elements known in the art. A "temperature-sensitive" vector is one which replicates normally at a low growth temperature (i.e., 28 C.) and will not replicate at a higher growth temperature (i.e., 42 C.) due to mutations at or near the origin of replication. An "imperfectly segregating" vector is one which is not stably inherited by new daughter cells at the time of cell division in the absence of selection pressure due to mutations within the vector sequence.

Host Cell: Refers to those cells capable of growth in culture and capable of expressing AexT protein and/or AexT fusion protein. The host cells of the present invention encompass cells in in vitro culture and include prokaryotic and eukaryotic cells, including insect cells. A host cell strain may be chosen which modulates the expression of the inserted sequences, or modifies and processes the gene product in the specific fashion desired. Expression from certain promoters can be elevated in the presence of certain inducers (i.e. temperature, small inducer molecules such as Beta-galactosides for controlling expression of T7 or lac promoters or variants thereof). The preferred host cell for the cloning and expression of the AexT protein and AexT fusion protein is a prokaryotic cell. An example of a prokaryotic cell useful for cloning and expression of the AexT protein of the present invention is *E. coli* BL21 (DE3).

Cell Culture: Refers to the growth of eukaryotic (non-bacterial) cells in a complex culture medium generally consisting of vitamins, buffers, salts, animal serum, and other nutrients.

Fusion Partner: Any DNA sequence cloned in frame to the 5' or 3' end of an ORF that results in transcription and translation of amino acid sequence added to the N- or C-terminus of the original protein.

Fusion Protein: The term fusion protein used herein refers to the joining together of at least two proteins, an AexT protein and a second protein. In some embodiments of the present invention, the second protein may be fused or joined to a third protein. In the present invention, examples of second proteins include any polypeptide that facilitates the following: expression, secretion, purification, condensation, precipitation, or any property which facilitates concentration or purification.

Promoter: A sequence of DNA to which the enzyme RNA polymerase binds (directly or through an intermediary protein, RNA polymerase binding protein) before initiation of transcription of the DNA into RNA. A promoter allows expression of a protein from the DNA coding sequence.

Variant: Any molecule in which the amino acid sequence, glycosylation, phosphorylation, and/or lipidation pattern, or any other feature of a naturally occurring molecule which has been modified covalently or non-covalently and is intended to include mutants. Some of the variants falling within this invention possess amino acid substitutions, deletions, and/or insertions provided that the final construct possesses the desired ability of AexT. Amino acid substitutions in AexT may be made on a basis of similarity in polarity, charge, solubility, hydrophobicity, hydrophilicity, and/or the amphipathic nature of the residues involved. Also included within the definition of variant are those proteins having additional amino acids at one or more of the C-terminal, N-terminal, and within the naturally occurring AexT sequence as long as the variant protein retains biological activity or the capability to act as an antigen and hence as a vaccine.

| Original Residue | Conservative Substitutions |
| --- | --- |
| Ala | ser |
| Arg | lys |
| Asn | gln; his |
| Asp | glu |
| Gln | asn |
| Glu | asp |
| Gly | pro |
| His | asn; gln |
| Ile | leu; val |
| Leu | ile; val |
| Lys | arg; gln; glu |
| Met | leu; ile |
| Phe | met; leu; tyr |
| Ser | thr |
| Thr | ser |
| Trp | tyr |
| Tyr | trp; phe |
| Val | ile; leu |

Table 1: More substantial changes in functional or other features may be obtained by selecting substitutions that are less conservative than those in Table 1, i.e., selecting residues that differ more significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. The substitutions which in general are expected to produce the greatest changes in protein properties will be those in which (a) a hydrophilic residue, e.g., seryl or threonyl, is substituted for (or by) a hydrophobic residue, e.g., leucyl, isoleucyl, phenylalanyl, valyl or alanyl; (b) a cysteine or proline is substituted for (or by) any other residue; (c) a residue having an electropositive side chain, e.g., lysyl, arginyl, or histidyl, is substituted for (or by) an electronegative residue, e.g., glutamyl or aspartyl; or (d) a residue having a bulky side chain, e.g., phenylalanine, is substituted for (or by) one not having a side chain, e.g., glycine. Variant peptides having one or more of these more substantial changes may also be employed in the invention, provided that biological activity or immunogenicity of AexT is retained.

More extensive amino acid changes may also be engineered into variant AexT peptides. These variant peptides will typically be characterized by possession of at least 40% sequence identity counted over the full length alignment with the amino acid sequence of their respective naturally occurring sequences using the alignment programs described below. In addition, these variant peptides will retain either biological activity or immunogenicity or both. Confirmation that an AexT peptide has biological activity may be achieved using the assay system described herein. Confirmation that an AexT peptide has immunogenic effect may be achieved by studies showing protection. Following confirmation that the AexT peptide has the desired activity or immunogenic effect, a nucleic acid molecule encoding the AexT peptide may be readily produced using standard molecular biology techniques. Where appropriate, the selection of the open reading frame will take into account codon usage bias of the bacterial, plant or other eukaryotic species in which the AexT peptide is to be expressed.

Inclusion body: Intracellularly confined, insoluble, protein-containing particles of bacterial cells comprised of either homologous or heterologous proteins. These particles are the reservoirs and consequence of overproduction of bacterial recombinant proteins. Inclusion bodies can be purified or semi-purified and used directly as protein antigens or can be solubilized by various procedures and used as soluble protein antigen preparations.

Alignment programs: Methods for aligning sequences for comparison purposes are well known in the art. Various programs and alignment algorithms are described in Smith and Waterman (1981), Needleman and Wunsch (1970), Pearson and Lipman (1988), Higgins and Sharp (1988, 1989), Corpet et al. (1988), Huang et al. (1992), Pearson et al. (1994). Altschul et al. (1990) presents a detailed consideration of sequence alignment methods.

The National Centre of Biotechnology Information (NCBI) Basic Local Alignment Search Tool BLAST; Altschul et al, 1990) is available from several sources, including the NCBI (Bethesda, MD) and on the Internet, for use in connection with the sequence analysis programs BLASTP, BLASTN, BLASTX, TBLASTN, TBLASTX. BLAST can be accessed at http://www.ncbi.nlm.nih.gov/BLAST/. A description of how to determine sequence identity using this program is available at http://www.ncbi.nln.nih.gov/BLAST/blast_help.html.

For comparisons of amino acid sequences of greater than 30 amino acids, the "BLAST 2 sequences" function in the BLAST program is employed using the BLASTP program with the default BLOSUM62 matrix set to default parameters, (open gap 11, extension gap 1 penalties). When aligning short peptides (fewer than 30 amino acids), the alignment should be performed sing the "Blast 2 Sequences" function employing the BLASTP program with the PAM30 matrix set to default parameters (open gap 9, extension gap 1 penalties). Proteins having even greater similarity to the reference sequences will show increasing percentage identities when assessed by this method, such as at least 45%, at least 50%, at least 60%, at least 70%, at least 75%, at least 80%, at least 85%, at least 90%, or at least 95% sequence identity.

II. Selection and Creation of Nucleic Acid Sequences Encoding the 50 kD AexT Protein, and use of AexT in recombinant and bacterin vaccines:

a. Growth and Purification of *Aeromonas* sp. and Plasmid Cloning Vectors.

*Aeromonas* strains (Table 1) were routinely cultured on blood agar plates (Trypticase soy agar supplemented with 0.1% $CaCl_2$ and 5% sheep blood) at 37° C. except for *A. salmonicida* which were grown at 20° C. *A. salmonicida* strain JF2267 was freshly isolated from an arctic char (*Salvelinus alpinus*) with typical furunculosis symptoms. The strain was identified as *A. salmonicida* by a routine diagnostic agglutination test using rabbit anti-*Aeromonas salmonicida* specific antiserum and by sequence analysis of the rrs (16S rRNA) genes (EMBL/GenBank Accession No. AF200329) as described by Kuhnert et al.

*Escherichia coli* strains XL1-blue (recA1 endA1 gyrA96 thi-1 hsdR17 supE44 relA1 lac [F' proAB lacI$^q$Z M15 Tn10 (Tet$^r$)]$^c$), and BL21(DE3) (F'dcm ompT hsdS($r_B$–$m_B$–) gal (DE3)) were used for cloning and expression of cloned genes respectively. Plasmid pBluescriptIISK-(Stratagene, La Jolla, Calif.) was used as cloning vector. Plasmid pETHIS-1 is a T7 promoter based expression vector and allows addition of poly-histidine tails at the N-terminal or at both N- and C-terminal ends of proteins (nucleotide sequence accession no. AF012911). *E. coli* strains were grown at 37° C. in Luria-Bertani broth (LB) supplemented when necessary with ampicillin (50 μg/ml) for selection and maintenance of recombinant plasmids. For blue-white selection with pBluescriptIISK-125 μM X-Gal (5-bromo-4-chloro-3-indolyl-D-galactopyranoside) and 1 mM IPTG (isopropyl-D-thiogalacto-pyranoside) were added.

*P. aeruginosa* ATCC 27853 was grown for 8 hrs on an LB-plate at 20° C. In order to induce ExoS and ExoT secretion cells were then incubated 18 hrs at 20° C. in 20 ml TSB (2.75 g/100 ml Trypticase-Soy broth without dextrose, 1% Glycerol, 0.1 M L-Glutamic acid, pH=7.3) supplemented with 10 mM NTA (Nitrilo-triacetic acid (Titriplex I) pH7.3) for chelation of $Ca^{2+}$ ions. Subsequently 5 mM PMSF were added and the culture was centrifuged for 15 min at 4'000 rpm. This protein fraction was used for further analyses on Western blots and for activity assays.

*A. salmonicida* ATCC 33658$^T$ was cultured at 20° C. in various media consisting of TSB supplemented with either 10 mM $CaCl_2$, or 0.01 to 1 mM EDTA, or 1 mM EDTA+1 mM PMSF, or 10 mM NTA, or 100 mM NTA, or 0.1 mM FeIII-$Cl_3$, or 0.1 mM FeII-$Cl_2$, or 0.1 mM EDDA (Ethylendiamine di(o-hydroxy-phinyl-acetic-acid)), or 20 mM Na-oxalate. A temperature shift experiment was performed by cultivating *A. salmonicida* ATCC 33658$^T$ in TSB at 20° C. to an $OD_{600}$ of 0.1 followed by further incubation over night at 32° C. Additionally various other *A. salmonicida* strains were cultured using the same conditions as described for *P. aeruginosa*. Culture supernatants and total cell protein extracts were analysed on western blots.

b. PCR, Cloning and Preparation of Gene Probes for ADP-Ribosylating Toxins.

PCR were carried out with a DNA thermal cycler (GeneAmp 9600; PE Biosystems, Norwalk, Conn.) in 50 μl reaction mixes containing 10 mM Tris-HCl, pH 8.3, 1.5 mM $MgCl_2$, 50 mM KCl, 0.25 μM forward and reverse primers, 0.5 units Taq polymerase, and 5 ng template DNA. The DNAs were amplified for 35 cycles with 30 s denaturation at 94° C., 30 s annealing at corresponding temperatures (Table 2), and 1 min extension at 72° C. For fragments above 1 kb, the extension time was extended by 1 min per kb. When DNA fragments were produced by PCR for subsequent cloning and expression, the expand long template PCR kit (Roche Molecular Biochemicals, Rotkreuz, Switzerland) containing polymerase with proof-reading capacity was used instead of Taq polymerase. In addition, an extension step of 7 min at 72° C. was added at the end of the last cycle in order to ensure full length synthesis of the different fragments. For the production of DIG-labelled probes PCR mixtures were supplemented with 40 μM digoxigenin-11-dUTP (Roche Molecular Biochemicals).

DNA fragment (called REXOS) corresponding to the catalytic portion of the *P. aeruginosa* exoS gene was amplified with the primer-pair REXOS-L and REXOS-R (Table 2) both containing EcoRI restriction site linkers. When genomic DNA of *P. aeruginosa* ATCC 27853 was used as template for PCR, 10% dimethyl sulfoxide were added. PCR-fragments were purified with the QIAquick PCR purification kit (QIAGEN, Basel, Switzerland). Plasmid pBluescriptIISK- and purified PCR fragments were digested with EcoRI and ligated for 2 hrs at room temperature before transformation of *E. coli* K-12 strain XL1-blue. After blue-white screening a white colony was selected and the prepared plasmid was sequenced in order to exclude cloning artefacts.

To get pure, plasmid-contaminant free probes, the cloned exoS derived fragment (REXOS) was excised with EcoRI, purified twice over agarose gels with the Jet-Sorb kit (Genomed GmbH, Bad Oeynhausen, Germany), and then used as template for PCR with the primers REXOS-L and REXOS-R (Table 2) for production of the DIG-labelled probe REXOS.

A DNA fragment (called RASEXOS) corresponding to the putative catalytic portion of *A. salmonicida* aexT gene was amplified with the primer-pair RASEXOS-L and RASEXOS-R (Table 2) and DIG-labelled. Genomic DNA derived from *A. salmonicida* ATCC 33658$^T$ (type strain) served as template.

All cloning procedures were essentially performed using standard protocols. DNA was extracted by the method of Pitcher et al. and manipulated using conventional methods. The $CaCl_2$ method was used for preparation of competent cells. Sequencing reactions were performed with a Taq Dye Deoxy Terminator cycle sequencing kit (PE Biosystems) and reaction products were analysed on an ABI Prism 310 genetic analyser (PE Biosystems).

Amplification of a DNA fragment containing the intergenic orfX-aexT region with the putative promoter region of aexT was performed by PCR using the primer pair BASEXOS693 and BASEXOS-250 (Table 2), genomic DNA of either the *A. salmonicida* ATCC 22658$^T$ or JF2267 strain as template and the Pwo DNA Polymerase (Roche Molecular Biochemicals). The intergenic region of the two genes orfX and aexT was subsequently sequenced with primer BASEXOS-250.

c. Construction of *A. salmonicida* Lambda Phage—Gen library.

Genomic DNA (0.1 μg) from *A. salmonicida* ATCC 33658$^T$ was digested partially with the restriction enzyme Sau3a to get fragments in the 3 to 4 kb range which were ligated to ZapExpress digested with BamHI (Pharmacia LKB, Biotechnology AB, Uppsala, Sweden) and packed into Lambda. A fresh culture of 200 μl of *E. coli* XL1-blue MRF'

(Pharmacia LYB) was resuspended in 10 mM $MgSO_4$ at an $OD_{600}$ of 1.0 and infected with the packed phages during 20 min at 37° C. Five ml Top Agarose (LB-broth supplemented with 0.7% Agarose) supplemented with IPTG and X-Gal were added, gently mixed and immediately poured onto an LB-Agar plate. Plates were incubated over night at 37° C. and plaques were lifted on nylon filters and screened using DIG-labelled probes. Positive plaques were cut out and stored over night at 4° C. in 0.5 ml SM-buffer (100 mM NaCl, 8 mM $MgSO_4$, 50 mM Tris pH7.5 and 0.01% gelatine) containing 20 µl chloroform. The in vivo excision of plasmids from selected phagemid plaques was done according the instructions of the ZAP express kit (Pharmacia LKB). Colonies with plasmids containing cloned fragments were isolated and mini-preps (Quiagen) were performed for plasmid purification.

d. Sequence Data Analyses.

Sequence alignment and editing were done with the software Sequencher (Gene Codes Corporation, Ann Arbor, Mich.). Sequence comparisons were done as described by Altschul et al. and sequences were aligned with the Wiscosin Package (Genetics Computer Group, Inc. [GCG], Madison, Wis.). The theoretical isoelectric pH (pI) and molecular masses of protein were calculated with the GCG software.

e. Southern Blot Analyses.

Southern blotting was done by alkaline transfer onto positively charged nylon membranes (Roche Molecular Biochemicals) with an LKB 2016 VacuGene vacuum blotting pump (Pharmacia LKB). Gels were depurinated for 10 min in 0.25 M HCl, and subsequent transfer was performed with 0.4 M NaOH. After blotting, filters were baked for 30 min at 80° C. under vacuum. After at least 1 h of prehybridisation, hybridisation was carried out in 5×SSC (1×SSC is 0.15 M NaCl plus 0.015 M sodium citrate)-1% blocking reagent (Roche Molecular Biochemicals)-0.1% N-lauroylsarcosine sodium salt-0.02% sodium dodecyl sulphate (SDS) at 68° C. over night, using DIG-labelled DNA fragments as probe. Filters were washed under nonstringent conditions twice for 5 min each with 50 ml of 2×SSC-0.1% SDS per 100 $cm^2$ at room temperature (20° C.), followed by medium-stringency washing twice for 15 min each with 50 ml of 0.2×SSC-0.1% SDS per 100 $cm^2$ at 20° C. The filters were then processed with phosphatase-labelled anti-DIG antibody according to the producer's protocol. Signals were produced with chemiluminescent substrate (CDP-Star; Roche Molecular Biochemicals) or with the chromogene substrate NBT-BCIP. Luminescence was detected on X-ray films.

f. Expression of His-Tailed Fusion Proteins.

E. coli BL21 (DE3) cells harboring recombinant pETHIS-1 plasmids with cloned genes were inoculated in 50 ml of LB-ampicillin at 37° C. to an $OD_{600}$ of 0.3 and induced by addition of 0.2 mM IPTG (final conc.) and subsequent growth for 3 hrs. The cells were sedimented by centrifugation at 4'000 rpm, resuspended in 5 ml of buffer pH7.9 containing 10 mM Tris-HCl, 1 M Urea, 250 mM NaCl, 2.5 mM Imidazole, 3 M Guanidium HCl, 0.2 mM PMSF and sonicated with a microtip for 20 min at 50% and 1-s interval in a Branson Sonifier 250 (Branson Ulatrasonics, Danbury, Conn.). This sonicated fraction was directly loaded onto a prewashed 1.25-ml-bed-volume Ni-NTA column (Quiagen) and washed once more with 5 ml binding buffer (2 M Urea, 20 mM Tris, 500 mM NaCl, 5 mM Imidazole, 60 mM Guanidium HCl pH7,9). addition of the poly-histidine proteins was performed with a 40-ml binding buffer-to-elution buffer (2 M Urea, 20 mM Tris, 500 mM NaCl, 500 mM Imidazole, 60 mM Guanidium HCl, pH7.9) gradient with a flow rate of 0.25 ml/min and collection of fractions of 1 ml with a HiLoad system (Pharmacia LKB). The fractions were analysed on SDS-10% acrylamide gels. Those containing the purified fusion protein were pooled and dialysed over night against 5 liters of 0.85% NaCl.

g. Immunisation of Rabbits with Purified Proteins.

Purified and dialysed recombinant protein solution (100 µg/ml) was mixed 1:1 with complete Freund's adjuvant (Difco Laboratories, Detroit, Mich.) and 2 ml of the emulsion were then injected subcutaneously to a rabbit. The rabbit was booster immunised with the same amount of protein emulsified with Freund's incomplete adjuvant 21 days later. On day 45 after the first immunisation, the rabbit was bled, and blood serum was prepared and stored at −20° C.

h. Infection of Fish Cell Cultures with A. salmonicida.

Rainbow trout (Oncorhynchus mykiss) gonad cells (RTG-2, ATCC CCL-55) were grown in 75 $cm^2$ tissue culture flasks (Techno plastic products AG, Trasadingen, Switzerland) at 22° C. in minimum essential medium (GibcoBRL Life Technologies, Basel, Switzerland) supplemented with 2 mM L-glutamine (GibcoBRL), 1× non essential amino acids (GibcoBRL), 3 g/l sodium bicarbonate and 10% foetal bovine serum. Three days before infection the cells were trypsinised and 4 million cells were seeded into a 25 $cm^2$ tissue culture flask. Monolayered RTG-2 cells were infected at a multiplicity of infection of 10:1 (bacteria:fish cells) with cells of A. salmonicida cultures resuspended in phosphate buffered saline (PBS) pH7.4. As control 100 µl of pure PBS pH7.4 were added. After 24 hrs of infection at 15° C. the fish cells were photographed under a green filtered phase contrast microscope (Axiovert 100, Zeiss, Jena, Germany). Detachment of the cells from the flask was obtained by shaking them by hand. The suspended cells were centrifuged for 5 min at 4'000 rpm. Lysis of the fish cells was performed in 100 µl distilled water with two subsequent freeze thawing steps and verified by microscopy. The lysed fish cells were used for further analyses on Western blots and for activity assays.

i. SDS-PAGE and Immunoblot Analyses.

Proteins were separated by SDS-10% polyacrylamide gel electrophoresis (SDS-PAGE) as described by Laemmli and transferred to a nitrocellulose membrane (Bio-Rad laboratories, Hercules, Calif). For immunoblotting, Western blots were blocked with 1% milk buffer for 30 min and then incubated with the rabbit antiserum (1:1500) or with sera (1:100) derived from diseased fish in milk buffer overnight at 4° C. After a thorough wash with water, the appropriate phosphatase-labelled conjugate (Goat anti-Rabbit IgG (H+L) [cat. no. 075-15061 or Goat anti-Trout Immunoglobulin [cat. no. 05-29-05], Kirkegaard & Perry, Gaithersburg, Md.) diluted 1:2000 or 1:500 respectively in milk buffer was added, and the reaction was visualised 90 min later by incubation with BCIP-NBT as the substrate.

j. ADP-Ribosyltransferase Assays.

ADP-ribosyltransferase assays contained 100 µM $^{14}C$-NAD (specific activity: 6 Ci/mol) and 0.2 M NaAc pH6 in a total of 20 µl. Either 0.1 mM soy bean trypsin inhibitor (SBTI, Roche Molecular Biochemicals) and 50 µg $ml^1$ wheat germ extract (Promega Corporation, Madison, Wis.) as source of FAS or 4 µl (approximately 200,000 cells) of non infected RTG2 fish cells were added as substrate. The reaction was started by adding 4 µl aliquots of supernatants of either P. aeruginosa ATCC 27853, A. salmonicida ATCC 33658 or *A. salmonicida* JF2267. An aliquot of pure growth medium was used for background determination. The reaction was performed at 20° C. for 1 hr and stopped by addition of 500 μl 10% trichloro acetic acid (TCA). The mixtures were blotted onto filters (GS 0.22 μm, Millipore, Bedford, Mass.) using a vacuum pump and washed 5 times with 0.75 ml 10% TCA. The filters were air dried and scintillation liquid Emulsifier scintillator plus, Packard instrument company, Meriden, Conn.) was added. Scintillation was detected as counts per minute (CPM) on a liquid scintillation counter (Wallac 1410, Pharmacia, Dübendorf, Switzerland). Experiments were performed in triplicate and scintillation was counted three times per experiment. Background counts were subtracted and results with their standard deviations are given in CPM (Table 3). Due to high background ADP-ribosyltransferase activity of the fish cells the activity of AexT in infected fish cells could not be measured.

EXAMPLES

The following examples are included to demonstrate preferred embodiments of the invention, and it will be appreciated by those skilled in the art, in light of this disclosure, that many changes can be made in the specific embodiments disclosed without departing from the scope of the invention.

1. Cloning and sequence analyses of aexT and its promoter. Analyses of different *Aeromonas* sp. with broad-range ADP-ribosylating toxin probes revealed a signal for a potential ADP-ribosyltransferase gene for *A. salmonicida* with probe REXOS which is derived from the catalytic domain of ExoS. This probe was used to screen a Lambda Phage gene library of *A. salmonicida* ATCC 33658$^T$. Three positive overlapping clones were found and joined together to a continuous DNA fragment of 2260 bp in length. The derived DNA sequence of this fragment revealed a complete ORF of 1428 bp showing high similarity with ExoT of *P. aeruginosa*. In analogy to ExoT, it was called *Aeromonas* exoenzyme T (AexT) and its corresponding gene aexT. The cloned fragment contains a further open reading frame, named ORFX which shows similarity to the sycE gene of *Yersinia* sp. and to ORF1 which precedes exoS of *P. aeruginosa* (FIG. 1). ORFX is preceded by a RBS and followed by a putative rho-independent transcription termination site. The sequenced DNA fragment encoding AexT and ORFX showed a high G+C content of 60%, which is above the average G+C content of *A. salmonicida* of 55%. The ORF representing aexT contains an ATG initiation codon and TGA stop codon. The 87 bp preceding the ATG show 71% identical nucleotide positions to the sequence preceding exoS and exoT in *P. aeruginosa*. The putative ribosomal binding site (RBS), AGAAG, is positioned 10 bp upstream of the ATG. The putative promoter sequences −10 box (TAGACT) and the canonical −35 box (CCGATA) of aexT are located at the same positions as those for exoS and exoT. Upstream of the promoter −10 and −35 box sequences there is a consensus binding site (TACAAAAA) similar to the one found upstream of exoS and exoT which is known in *P. aeruginosa* to be bound by the transcriptional regulator ExsA. An inverted repeat (AACGGACACCCtcGGGTGTC-CGTT) is located 25 bp downstream of the stop codon of the aexT gene. It has the same stem sequence (CGGACAC) as inverted repeats of the putative transcription termination sites of exoS and exoT.

2. Structural analyses of the AexT. The amino acid sequence for AexT was deduced from the nucleotide sequences using the universal genetic code. AexT has a calculated pI of 5.13 and a molecular mass of 50.1 kDa Blast searches revealed similarity of AexT with ExoT and ExoS over the whole length. In addition similarity with the YopE cytotoxin of *Yersinia pseudotuberculosis* (EMBL/GenBank Accession No. P08008), *Y. pestis* (Acc. No. P31493) and *Y. enterocolitica* (Acc. No. M34280) was found within the N-terminal 210 amino acids of AexT (FIG. 1). Gap comparisons with the amino acid sequence of AexT with ExoT and ExoS revealed AexT to be identical in 62.8% with ExoT (57.9% with ExoS) and similar in 67.5% with ExoT (62.8% with ExoS) of the positions (FIG. 1) with a gap of 25 aa in length, which separates the N-terminal from the C-terminal domain. Gap comparisons of ExoT with ExoS showed them to be identical in 75.1% and similar in 77.7% of the positions. The N-terminal domain of AexT revealed 33.5% identical and 37.4% and similar amino acid positions compared to the cytotoxin YopE of *Y. pseudotuberculosis* and 26.8% identical and 32.8% similar amino acids to YopE of *Y. pestis* (FIG. 1). The biglutamic acid active site (GD-EQEILYNK) found for various ADP-ribosylating toxins is also conserved within the C-terminal domain of AexT (FIG. 1).

3. Specificity of aexT genes for *A. salmonicida*. Southern blot analyses of genomic DNA of various *Aeromonas* sp. (Table 1) with DIG labelled probe for aexT(RASEXOS) revealed a single copy of aexT with a size estimated to be approximately 3 kb for all *A. salmonicida* strains tested (Table 1). None of the other analyzed *Aeromonas* strains showed hybridisation signals with the aexT probe under these hybridisation conditions, butt this does not rule out the possibility that other strains of *Aeromonas* or other bacterial genera may possess homologues of aexT.

4. Production and characterisation of recombinant AexT. In order to characterize biochemically the AexT protein and to produce polyclonal, monospecific antibodies directed against AexT, we have expressed poly-histidine tailed AexT, named AexT-His, in recombinant *E. coli* K-12 strains. The entire coding part inclusive the stop codon of the aexT gene was amplified by PCR using primers BASEXOSH8L and BASEXOSH8R and genomic DNA of *A. salmonicida* as template. The purified PCR product was digested with restriction enzymes EcoRI and SpeI and cloned into EcoRI and SpeI digested vector pETIHS-1 to obtain plasmid pJF-FASAexT-His, encoding N-terminally poly-histidine tailed AexT (AexT-His) under the control of the T7 promoter. For the expression of the aexT-His gene, plasmid pJFFASAexT-His was transformed into *E. coli* strain BL21(DE 3) as described in Materials and Methods. Biochemical analysis of purified and renatured recombinant AexT-His revealed that it possessed ADP-ribosylating activity (Table 3). Monospecific polyclonal antibodies against AexT were obtained by immunisation of a rabbit with purified AexT-His protein as described for other poly-histidine tailed proteins. Anti-AexT antibodies reacted on immunoblots with purified AexT-His. It also cross reacted with the 49 kDa and 53 kDa proteins in supernatant from a culture of *P. aeruginosa* ATCC 27853, representing the ExoS and ExoT protein toxins as expected from sequence similarities with AexT.

Figure 2:

5. Expression of AexT in *A. salmonicida*. The expression of AexT by *A. salmonicida* type strain ATCC 33658$^T$, which seems to have lost its pathogenicity, and of *A. salmonicida* field strain JF2267, which was freshly isolated from a diseased arctic char and which still possesses its virulence, was assessed by immunoblots with anti AexT-His antibodies. Neither supernatants nor the cell pellets of the type strain ATCC 3365$^T$ grown under various conditions showed any specific reactions on immunoblots with monospecific, polyclonal anti-AexT antibodies. In contrast supernatants and cell pellets of *A. salmonicida* strain JF2267 grown in TSB supplemented with 10 mM NTA reacted on immunoblots with anti-AexT-His antibodies (FIG. 2). When NTA was omitted in the growth media, AexT protein in strain *A. salmonicida* JF2267 only was found in the cell pellet but not in supernatants. When *A. salmonicida* strain JF2267 was analysed during infection of RTG-2 fish cells, a specific reaction on immunoblots using anti-AexT-His antibodies with a 56 kDa protein corresponding to AexT was found. This indicates that strain JF2267 required contact with fish cells or depletion of $Ca^{2+}$ ions (or other cations) to induce the production or protection of AexT. However, no AexT could be detected for *A. salmonicida* type strain ATCC 33658 under the same conditions (FIG. 2). ADP-ribosyltransferase activity was determined in culture supernatants of *A. salmonicida* strains and as control of *P. aeruginosa*, grown under $Ca^{2+}$ depleted conditions. *A. salmonicida* field strain JF2267 showed ADP-ribosyltransferase values slightly above background and no activity could be measured in *A. salmonicida* ATCC $33658^T$, while *P. aeruginosa* showed high activity (Table 3). ADP-ribosyltransferase could not be determined in infected fish cells due to high background activity.

Figure 3:
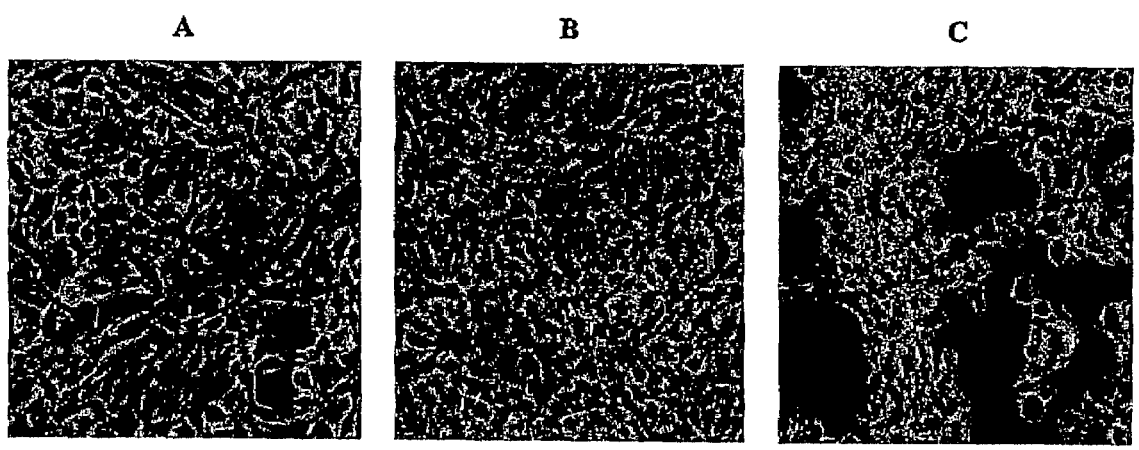

Infection of RTG-2 cells with freshly cultured *A. salmonicida* strain JF2267 caused a toxic effect showing characteristic cell rounding, detachment and lysis of cells within 24 hours (FIG. 3C) whereas the cells infected with *A. salmonicida* type strain ATCC $33658^T$ (FIG. 3B) or the control cells incubated with pure PBS (FIG. 3A) showed no morphological changes at all. Infection of fish cell culture with *A. salmonicida* JF2267 also induced the production of the AexT protein which reacted with anti-AexT-His antiserum. Similar morphological changes have been reported for cells infected with ExoS producing *P. aeruginosa*. The sera raised against AexT-His also showed cross-reactivity with ExoS and ExoT produced by *P. aeruginosa*. Similar cross-reactivity was found for anti-exoenzyme S IgG which reacted with both ExoS and ExoT. The fact that AexT is produced specifically in contact with fish cells (FIG. 3C) or in $Ca^{2+}$ depleted medium (FIG. 2), which is believed to act as pseudo-trigger to induce aexT, suggests the protein to be produced specifically during infection and hence to play an important role in pathogenicity. Interestingly, *A. salmonicida* type strain ATCC $33658^T$ does not affect the morphology of RTG-2 cells. It seems to have lost the ability of producing cell contact induced AexT probably due to repeated passages on growth medium.

In order to determine whether the significant differences in AexT production and toxic effect between *A. salmonicida* isolate JF2267 and type strain ATCC 33658 could be due to mutations within the putative promoter regions of their respective aexT genes, the intergenic regions between orfX and aexT were sequenced and found to be identical. Thus, the alteration responsible for the loss of AexT production in the type strain seems to reside outside the aexT operon. Nevertheless, both *A. salmonicida* strains ATCC $33658^T$ and JF2267 have the same haemolytic activity as estimated on blood agar plates implying that the toxic effect for RTG-2 cells is not due to the *A. salmonicida* haemolysins but rather to production of AexT in strain JF2267. The loss of expression of aexT as observed in *A. salmonicida* type strain ATCC 33658 is a frequent event in this species, and may explain the currently observed variations in virulence and also differences in efficacy of protection of whole cell antigen vaccines.

6. Recombinant AexT Vaccine Trial (See Appendix A)

7. Testing of different *A. salmonicida* bacterin vaccines in Altantic salmon (*Salmo salar*) (See Appendix B)

The current data indicate that AexT of *A. salmonicida* is a determinative virulence factor of this pathogen. While particular elements, embodiments and applications of the present invention have been shown and described, it will be understood, of course, that the invention is not limited thereto, since modifications may be made by those skilled in the applicable technologies, particularly in light of the foregoing description The appended claims include within their ambit such modifications and variants of the exemplary embodiments of the invention described herein as would be apparent to those skilled in the applicable technologies.

TABLE 1

*Aeromonas* strains used

| Species | Strain[a] | aexT positive[b]/ strains tested |
|---|---|---|
| A. salmonicida | ATCC $33658_T$ | 1/1 |
| A. salmonicida | JF2267[c] | 1/1 |
| A. salmonicida | field isolates | 10/10 |
| A. bestiarum | CDC 9533-76 | 0/1 |
| A. bestiarum | field isolates | 0/2 |
| A. caviae | ATCC 15468 | 0/1 |
| A. caviae | field isolates | 0/3 |
| A. encheleia | DSM 11577 | 0/1 |
| A. eucrenophila | NCMB 74 | 0/1 |
| A. eucrenophila | field isolate | 0/1 |
| A. hydrophila | ATCC 7966 | 0/1 |
| A . hydrophila | field isolates | 0/15 |
| A. jandaei | ATCC 49568 | 0/1 |
| A. media | ATCC 33907 | 0/1 |
| A. schubertii | ATCC 43700 | 0/1 |
| A. schubertii | field isolate | 0/1 |
| A. sobria | CIP 7433 | 0/1 |
| A. trota | ATCC 49657 | 0/1 |
| A. trota | field isolate | 0/1 |
| A. veronii | ATCC 35624 | 0/1 |
| A. veronii | field isolates | 0/4 |

[a]ATCC, American Type Culture Collection, Rockville, Md.; JF, Joachim Frey, University of Berne, Switzerland; CDC, Center for Disease Control, Atlanta, Georgia; DSM, Deutsche Sammlung von Mikroorganismen und Zellkulturen GmbH, Braunschweig, Germany; NCMB, National Collection of Marine Bacteria, Aberdeen, Scotland; CIP, Collection of the Institut Pasteur, Paris, France.

[b]Determined by Southern blotting using DIG labelled RASEXOS as probe.

[c]JF2267 was isolated freshly from an arctic char with typical symptoms of furunculosis. Identification was done phenotypically and by 16s rDNA gene sequencing.

TABLE 2

Oligonucleotide primers

| Name (SEQ ID NO) | Sequence[a] 5' to 3' | Position | Annealing temp ° C. |
|---|---|---|---|
| EXOS-L (SEQ ID NO:12) | cgcgaattcACTGGCTGGGCAAACTG | 1128-1144[b] | 52 |
| EXOS-R (SEQ ID NO:13) | cgcgaattCCCGCTGACATCGATTC | 2034-2019[b] | 52 |
| RASEXOS-L (SEQ ID NO:14) | GGCGCTTGGGCTCTACAC | 1537-1554[c] | 60 |
| RASEXOS-R (SEQ ID NO:15) | GAGCCCGCGCATCTTCAG | 2089-2072[c] | 60 |
| BASEXOSH8L (SEQ ID NO:16) | cgcgaattCGGCGAAACATCACAAGA | 645-662[c] | 59 |
| BASEXOSH8R (SEQ ID NO:17) | ggactagTCCCGCCAGCATAAAAAAC | 2165-2147[c] | 59 |
| BASEXOS693 (SEQ ID NO:18) | AGGCTCAACGTTAACTTCGC | 1432-1413 | 58 |
| BASEXOS-250 (SEQ ID NO:19) | AGAGGGAGAGAAACAGCTGG | 427-446 | 58 |

[a]Lowercase letters indicate nucleotides added to create restriction enzyme recognition sites (underlined) for cloning.
[b]Based on nucleotide sequence L27629 of *P. aeruginosa*
[c]Based on nucleotide sequence of *A. salmonicida*

TABLE 3

Determination of ADP-ribosyltransferase activity

|  | cpm A) | std. dev.[C] |
|---|---|---|
| *A. salmonicida* | | |
| ATCC 33658[T], culture supernatant | 0 | ±10 |
| JF2267, culture supernatant | 5 | ±12 |
| AexT-His | 123 | ±11 |
| *P. aeruginosa* ATCC 27853 | | |
| culture supernatant (ExoS + ExoT) | 4286[B)] | ±125 |

A) Mean values corrected for background. Experiments were performed in triple and scintillation was measured three times per experiment.
[B)]The proportion of ADP-ribosyltransferase activity of ExoT is estimated to be approximately 0.2% corresponding to 8 cpm under these conditions.
[C)]Standard deviation in cpm Appendix A Recombinant AexT Vaccine Trial Materials:

Vaccine Formulations:
1. The AexT vaccine was formulated using recombinant, Histidine-tagged AexT resuspended in 10 mM phosphate buffer, pH 7.0, to 200 µg/mL. Four parts of this protein solution were mixed with one part oil adjuvant for a final AexT concentration of 150 µg/mL. The dose for testing was 0.1 mL, or 15 µg/fish.
2. The commercial comparator vaccine was serial 4-13 of the vaccine MultiVacc4 (Bayotek International Ltd.)
3. The placebo (control) vaccine consisted of phosphate buffered saline(PBS) (10 mM phosphate, 150 mM NaCl, pH 7.2).
4. All vaccines were maintained at 4° C. until use.

Methods

Trial Design:

Fish (rainbow trout *Oncorhynchus mykiss*) that have been determined to be pathogen free and are at least 15 g in size are held for at least one-week pre vaccination for acclimation purposes. During the acclimation period the fish are offered 1% body weight in salmonid fish food every day, however they are denied food 24 hours pre and post-vaccination.

At least 50 fish are vaccinated 0.1 mL of AexT vaccine via intra-peritoneal (IP) injection, or 0.2 mL of the commercial vaccine MultiVacc4. At the same time a group of at least 50 fish from the same stock are mock vaccinated with 0.1 mL of PBS. Vaccinated fish are then held for a period of at least 350-degree days to allow specific immune response generation in an acclimation tank with a continuous flow of water at a temperature of 12-13° C. The fish are offered 1% body weight in salmonid fish food daily until 24 hours pre-challenge and post-challenge.

After at least 350-degree days post vaccination 50 fish per group were challenged by IP injection with a pre-determined concentration of virulent *Aeromonas salmonicida*. The dosage depends on the source of the fish and the water temperature (this is determined empirically immediately prior to challenge of test fish). The identical procedure is performed with the placebo vaccinated control fish. The fish are observed daily for mortality for 21 days post challenge and the cause of mortality assessed and examined to ensure that mortality is attributed to the challenge organism. After 24 hours post-challenge the fish are again offered 1% body weight in salmonid fish feed daily. Tanks are maintained with a continuous flow of water at a temperature of 12-13° C. For a challenge series to be considered satisfactory; all challenge groups must meet the following criteria:

1. At least 70% of the non-immunized controls must die within 21 days of challenge.
2. A relative percent survival (RPS) of no less than 25% must be achieved for the challenge disease before a vaccine is considered even partially efficacious for this disease.

$$RPS = [1-(\% \text{ mortality vaccinates}/\% \text{ mortality controls})] \times 100$$

Specificity of Immunity was Confirmed by Challenge with *Vibrio anguillarum*

Developed from: The Rules Governing Medicinal Products in the European Union, Volume VII, Guidelines for the testing of veterinary medicinal products. 1994. Specific Requirements for the Production and Control of Live and Inactivated Vaccines Intended for Fish. Section 3.2. Potency.

Results

| Group | % Mortality | RPS |
|---|---|---|
| PBS | 82 | — |
| AexT | 37 | 55 |
| MultiVacc4 | 30 | 63 |

1. There was a strong challenge with 82% control mortalities.

*Vibrio anguillarum* immersion challenge shows that the AexT protects specifically against *A. salmonicida* (93% mortality in AexT vaccinates compared to 15% for commercial vibrio vaccine vaccinates). Challenged survivors of the A sal challenge (and salines) with *Vibdio anguillarum* type 1. The challenge organism used was *Vibrio anguillarum* serotype 01 at an O.D. of 0.5 (~8.0×10E8 CFU/mL). This indicates that the immune response is specific.

Appendix B

Testing of different *Aeromonas salmonicida* bacterin vaccines in Atlantic salmon (*Salmo salar*)

Purpose: Determination of the efficacy of *Aeromonas salmonicida* bacterins produced by different methods in Atlantic salmon (*Salmo salar*), and a correlation between protection and AexT production.

Materials:

Methods:

*A. salmonicida* Vaccine Preparations:
 1. Bacterin Preparations: A standard *A. salmonicida* vaccine master working seed from Microtek International (1998) Ltd., MSW26, was used for all vaccine preparations. The starter culture for each fermentation was derived from 25 mL of Tryptic Soy Broth inoculated with a single I mL frozen (−80° C.) aliquot of MSW26 followed by incubation with shaking (18° C. at 100 rpm) for 36 hours. This primary starter culture was used to inoculate a 10 L fermenter
    a. Bacterin 1: Bacterin 1 was prepared by fermented culture incubated at 20° C. ±2° C., with sufficient agitation and aeration to maintain the dissolved oxygen ($DO_2$) at above approximately 25%. The pH is maintained between 6.5 and 7.5 (pH controlled by the addition of a $NH_4OH$ solution and aqueous KOH). The media is Tryptic soy broth with glucose at 1%. During fermentation a concentrated sterile solution of glucose is fed into the fermenter. Glucose is fed to maintain a glucose concentration of between 1.0 g/l to 10.0 g/l. Concentrated, sterile solutions of TSB without glucose are also fed at 1-2% of the culture volume into the fermenter. The TSB without glucose is fed at $OD_{650nm}$ of between 2 and 3, again at $OD_{650nm}$ of between 4 and 5. The fermenter culture is fed periodically with a concentrated sterile solution of glucose to maintain a glucose concentration of between 1.0 g/l to 10.0 g/l until the $OD_{650nm}$ reaches approximately 8.0. The culture is fed with a concentrated solution of TSB without glucose to an $OD_{650nm}$ of approximately 10-12. The pH is maintained between 6.5 and 7.5 (pH controlled by the automatic addition of KOH and $H_2SO_4$). The *A. salmonicida* culture is inactivated by the addition of 7.0 mL/l±0.7 mL/l formalin. Aeration to the fermenter is stopped. The inactivated culture is agitated in the fermenter for a period of 1 hour at 20° C.±2° C. The inactivated bacterial culture will then be pumped or gravity fed directly from the fermenter into holding vessels and stirred for a further 24 hour inactivation step. The Inactivated bacterial culture was then held at 4° C. for further processing and formulation.
    b. Bacterin 2 and 3: Bacterins 2 and 3 were prepared as duplicates by fermented culture incubated at 20° C.±2° C., with sufficient agitation and aeration to maintain the dissolved oxygen ($DO_2$) at approximately 15-25%. The pH is maintained between 6.9 and 7.1 (pH controlled by the addition of a $NH_4OH$ solution and H2SO4). The media is Tryptone (1.5%), Yeast extract (0.5%), Glycerol (1%), NaCl (0.5%), Glutamate (100 mM), and Citrate (20 mM). During fermentation a concentrated sterile solution of Tryptone (15%), Yeast extract (5%), NaCl (0.5%), Glycerol (10%), Glutamate (100 mM), and Citrate (20 mM) is fed into the fermenter. The fermenter culture is fed continuously with this concentrated sterile solution to maintain a stable $pO_2$. The resulting *A. salmonicida* culture is inactivated by the addition of 7.0 mL/l±0.7 mL/l formalin. Aeration to the fermenter is stopped. The inactivated culture is agitated in the fermenter for a period of 1 hour at 20° C.±2° C. The inactivated bacterial culture will then be pumped or gravity fed directly from the fermenter into holding vessels and stirred for a further 24 hour inactivation step. The inactivated bacterial culture was then held at 4° C. for further processing and formulation.
 2. Vaccine Formulations: Vaccines were formulated using washed cells (performed by centrifugation at 1500×g) resuspended in 10 mM phosphate buffer, pH 7.0, to 10 $O.D._{650}$. Each test vaccine based on the bacterins 1 through 3 were formulated by mixing 1 part adjuvant with 5 parts washed bacterin cells and 4 parts 10 mM phosphate pH 7. All vaccines were maintained at 4° C. until use.
 3. Western Immunoblotting: Prior to electrophoresis bacterin samples containing equivalent cellular mass were solublized by mixing with equal amounts of sample loading buffer followed by boiling for 5 minutes. The prepared samples were then separated on a 12% polyacrylamide gel by the discontinuous gel method of Laemmli (1970). Two identical gels were prepared. One gel was stained for total protein with Coomassie Blue and dried on cellulose film. The proteins from the second gel were electrophoretically transferred to nitrocellulose membrane as described by Towbin et al. (1979). Following transfer, the membrane was blocked with phosphate-buffered saline (pH 7.2) and 0.1% Tween-20 (PBS-Tween) with 2% BSA. The blot was probed with polyclonal rabbit anti-AexT at a 1:500 dilution in PBS-Tween+1% BSA for 2 h and washed with PBS-Tween. Alkaline phosphatase-conjugated polyclonal goat anti-rabbit antibody (Caltag) was applied to the membrane at a 1:2500 dilution in TBBT for 2 h, washed In TBBT. The transblot was then developed using NBT and BCIP as a colour reagent system at pH 9.4.

A. salmonicida Immunity: Fish (rainbow trout *Oncorhynchus mykiss* and/or Atlantic. salmon *Salmo salar*) that have been determined to be pathogen free and are at least 15 g in size are held for at least one-week pre vaccination for acclimation purposes. During the acclimation period the fish are offered 1% body weight in salmonid fish food every day, however they are denied food 24 hours pre and post-vaccination.

At least 50 fish are vaccinated 0.2 cc of vaccine via intra-peritoneal (IP) injection, at the same time a group of at least 50 fish from the same stock are mock vaccinated with 0.2 cc of saline. Vaccinated fish are then held for a period of at least 350-degree days to allow specific immune response generation in an acclimation tank with a continuous flow of water at a temperature of 12-13° C. The fish are offered 1% body weight in salmonid fish food daily until 24 hours pre-challenge and post-challenge.

After at least 350-degree days post vaccination 50 fish are challenged by immersion in, or IP injection with, a pre-determined concentration of virulent *Aeromonas salmonicida*. The dosage depends on the source of the fish and the water temperature (this is determined empirically immediately prior to challenge of test fish). The identical procedure is performed with the mock-vaccinated control fish. The fish are observed daily for mortality for 21 days post challenge and the cause of mortality assessed and examined to ensure that mortality is attributed to the challenge organism. After 24 hours post-challenge the fish are again offered 1% body weight in salmonid fish feed daily. Tanks are maintained with a continuous flow of water at a temperature of 12-13° C. For a challenge series to be considered satisfactory; all challenge groups must meet the following criteria:

1. At least 70% of the non-immunized controls must die within 21 days of challenge.
2. A relative percent survival (RPS) of no less than 25% must be achieved for the challenge disease before a vaccine is considered even partially efficacious for this disease.

$$RPS = [1 - (\% \text{ mortality vaccinates}/\% \text{ mortality controls})] \times 100$$

Developed from: The Rules Governing Medicinal Products in the European Union, Volume VII, Guidelines for the testing of veterinary medicinal products, 1994. Specific Requirements for the Production and Control of Live and Inactivated Vaccines Intended for Fish. Section 3.2. Potency.

Data:

See Excell file

Western Immunoblot:

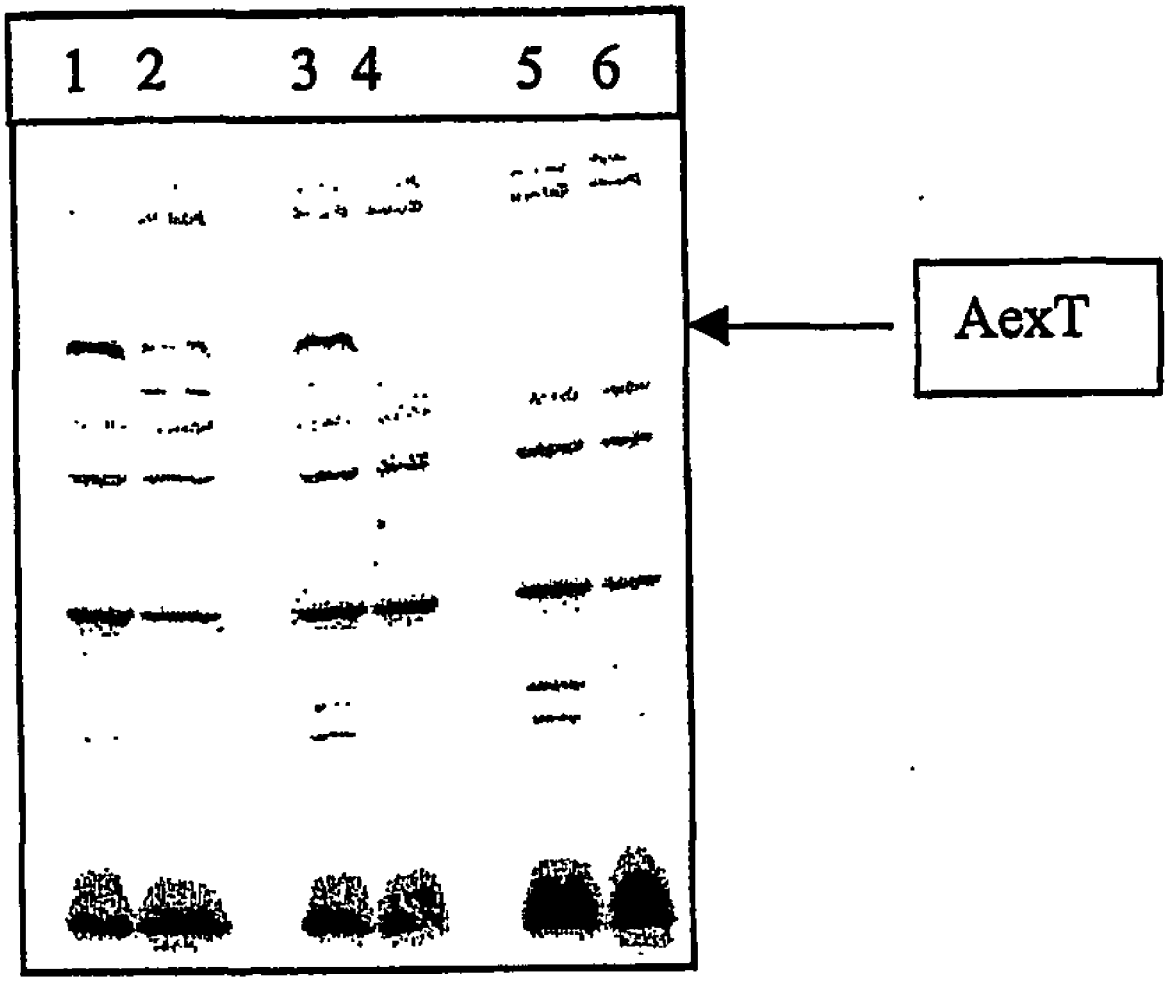

Gel Contents:

Lane 1: Bacterin 2 cell pellet; Lane 2: Bacterin 2 culture supernatant; Lane 3: Bacterin 3 cell pellet; Lane 4; Bacterin 3 culture supernatant; Lane 5: Bacterin 1 cell pellet; Lane 6: Bacterin 1 culture supernatant.

Conclusions:

Vaccines for furunculosis (the disease caused by A. salmonicida) are more efficacious if AexT is induced using specific culture conditions. The presence of AexT in a bacterin can be determined by Western Immunoblotting and developing with anti-AexT antibodies.

A. sal Vaccinate Challenge

50 RBT of approx. 12 g were vaccinated with 2 vaccine candidates.
Saline controls were additionally vaccinated.
350 degree days post-vaccination, all groups were challenged with *A. salmonicida*
Challenge Culture Information OD650 nm = 0.201 = 1.0E+08 cfu/mL
Used 0.1 mL of 3.3E+05 cfu/mL (washed cells) per fish
A. sal: washed in 0.85% saline, final titre of 3.3E+05 cfu/mL Number of RBT remaining

| | | TANKS | | | |
|---|---|---|---|---|---|
| Date | Days | C1 Saline | C2 Bacterin 1 no AexT | B1 Bacterin 2 + AexT | B2 Bacterin 3 + AexT |
| 26-Apr-01 | 0 | 50 | 50 | 45 | 50 |
| 27-Apr-01 | 1 | 50 | 50 | 45 | 50 |
| 28-Apr-01 | 2 | 50 | 50 | 45 | 50 |
| 29-Apr-01 | 3 | 28 | 48 | 45 | 49 |
| 30-Apr-01 | 4 | 9 | 36 | 45 | 46 |
| 01-May-01 | 5 | 8 | 31 | 45 | 45 |
| 02-May-01 | 6 | 4 | 26 | 44 | 44 |
| 03-May-01 | 7 | 4 | 26 | 43 | 43 |
| 04-May-01 | 8 | 4 | 26 | 42 | 42 |
| 05-May-01 | 9 | 4 | 21 | 41 | 41 |
| 06-May-01 | 10 | 4 | 21 | 41 | 41 |
| 07-May-01 | 11 | 3 | 21 | 41 | 41 |
| 08-May-01 | 12 | 2 | 21 | 41 | 41 |
| 09-May-01 | 13 | 2 | 21 | 41 | 41 |
| 10-May-01 | 14 | 2 | 21 | 41 | 41 |
| 11-May-01 | 15 | 2 | 21 | 41 | 41 |
| 12-May-01 | 16 | 2 | 21 | 41 | 41 |
| 13-May-01 | 17 | 2 | 21 | 41 | 41 |
| 14-May-01 | 18 | 2 | 21 | 41 | 41 |
| 15-May-01 | 19 | 2 | 21 | 41 | 41 |
| 16-May-01 | 20 | 2 | 21 | 41 | 41 |
| 17-May-01 | 21 | 2 | 21 | 41 | 41 |
| Gross % survival | | 4.00 | 46.00 | 91.11 | 82.00 |
| Gross % mortality | | 96.00 | 54.00 | 8.89 | 18.00 |
| Gross RPS | | 0 | 44 | 91 | 81 |

The invention claimed is:

1. An isolated nucleic acid molecule, encoding a polypeptide having at least 95% amino acid sequence identity to the amino acid sequence of SEQ ID NO:2, wherein the polypeptide has ADP-ribosyltransferase activity, or the fully complementary sequence thereof.

2. The isolated nucleic acid molecule of claim 1, wherein said molecule comprises the nucleotide sequence of SEQ ID NO:1, or a fully complementary sequence thereof.

3. A vector comprising the nucleic acid molecule of claim 1.

4. A vector comprising the nucleic acid molecule of claim 2.

5. A host cell comprising the vector of claim 3.

6. A host cell comprising the vector of claim 4.

7. The host cell of claim 5, wherein said host cell is a prokaryotic cell.

8. The host cell of claim 6, wherein said host cell is a prokaryotic cell.

9. A method for recombinant expression of AexT, the method comprising culturing the host cell of claim 5 under suitable conditions so as to give rise to expression thereof.

10. A method for recombinant expression of AexT, the method comprising culturing the host cell of claim 6 under suitable conditions so as to give rise to expression thereof.

11. An isolated nucleic acid molecule, or a fully complementary sequence thereof, that hybridized under a stringent condition to a nucleotide sequence or its full complement, wherein the nucleotide sequence encodes a polypeptide having the amino acid sequence of SEQ ID NO:2, wherein the stringent condition comprises washing at 20° C. with 0.2×SSC and 0.1% SDS.

* * * * *

SEQUENCE LISTING

<160> NUMBER OF SEQ ID NOS: 5

<210> SEQ ID NO 1
<211> LENGTH: 1428
<212> TYPE: DNA
<213> ORGANISM: Aeromonas salmonicida

<400> SEQUENCE: 1

```
atgcagattc aagcaaacac cgtcggcaca caggccgtcg ctcaccacag tgatgccacg      60
accggagttg gccggatggg tcagatggag gcgcgtcagg tcgccaccgg acaagatgcg     120
atcctgctgg gcagtcgcag cgaaccgcaa aaagggcagg ggctgctctc gcgactgggg     180
gcccagctgg cccgcccgtt cgtggccatc aaagagtgga tcagcaacct gctgggacg      240 gacaagcgtg ccgctgcgcc gaaggcgcaa accgccgttt ccccgagga tcttcagcga      300 ctgatgaagc aggctgcatt tggtagctcg ctgggtggct tcgccaaggc ggacgtgttg     360
aacaacatca caggcgaaca attgggcaag gatcacgcca gtctggcgac cggcaatggc     420
```

-continued

```
cccctgcgct ctctctgcac cgcgttgcag gccgttgtca taggatctca gcaaccgcaa      480
ctccgggagt tggctaccgg gctgctggcc cgccccatcg ccggtatccc gctccagcag      540
tgggggtcgg taggcggcaa ggtgaccgag ctgctcacca gcgccccccc cgaactgttg      600
aaggaggcta tgagccagct acacaccgcg atgggtgaag ttgccgacct gcagcgcgct      660
gtaaaggcaa agttgctgg cgaaccggcg cgaagcgcga ccacagcggc cgctgtggcg      720
ccgctccaaa gcggtgagag cgaagttaac gttgagcctg ccgacaaggc gctggcagag      780
ggcttgcagg agcaattcgg cctggaggcc gagcaatatc tgggtgaaca gccccacggt      840
acttacagcg atgctgaagt gatggcgctt gggctctaca ccaacggcga ataccagcac      900
ctgaatcgct cgctgcgtca ggaaaagcag ctggatgcag gcaagcgtt gatcgatcag      960
ggtatgtcca ccgcttttga aaaagtacc cccaccgagc agttgatcaa gaccttccgc     1020
ggtacccacg gcggcgatgc gttcaacgag gtggcagagg ggcaagtcgg tcatgatgtc     1080
gcttatcttt ccacctctcg ggatcccaag gtggcaacca actttggtgg ttcaggctcc     1140
atatccacga tatttggccg ctcgggatc gatgtcagcg acatatccgt tgaaggtgac     1200
gagcaggaga tcctctataa caaagagact gatatgcggg tattgctcag tgccaaagat     1260
gaacggggcg tcacccggcg ggtactggaa gaggcctcgc tggggggaaca aagcggccac     1320
agcaaggggc tgctggacgg gctggatctg gcaagaggag cgggcggtgc cgacaagccg     1380
caagagcaag atatccgtct gaagatgcgc gggctcgatt tggcgtga                 1428
```

<210> SEQ ID NO 2
<211> LENGTH: 475
<212> TYPE: PRT
<213> ORGANISM: Aeromonas salmonicida

<400> SEQUENCE: 2

```
Met Gln Ile Gln Ala Asn Thr Val Gly Thr Gln Ala Val Ala His His
1               5                   10                  15

Ser Asp Ala Thr Thr Gly Val Gly Arg Met Gly Gln Met Glu Ala Arg
            20                  25                  30

Gln Val Ala Thr Gly Gln Asp Ala Ile Leu Leu Gly Ser Arg Ser Glu
        35                  40                  45

Pro Gln Lys Gly Gln Gly Leu Leu Ser Arg Leu Gly Ala Gln Leu Ala
    50                  55                  60

Arg Pro Phe Val Ala Ile Lys Glu Trp Ile Ser Asn Leu Leu Gly Thr
65                  70                  75                  80

Asp Lys Arg Ala Ala Ala Pro Lys Ala Gln Thr Ala Val Ser Pro Glu
                85                  90                  95

Asp Leu Gln Arg Leu Met Lys Gln Ala Ala Phe Gly Ser Ser Leu Gly
            100                 105                 110

Gly Phe Ala Lys Ala Asp Val Leu Asn Asn Ile Thr Gly Glu Gln Leu
        115                 120                 125

Gly Lys Asp His Ala Ser Leu Ala Thr Gly Asn Gly Pro Leu Arg Ser
    130                 135                 140

Leu Cys Thr Ala Leu Gln Ala Val Val Ile Gly Ser Gln Gln Pro Gln
145                 150                 155                 160

Leu Arg Glu Leu Ala Thr Gly Leu Leu Ala Arg Pro Ile Ala Gly Ile
                165                 170                 175

Pro Leu Gln Gln Trp Gly Ser Val Gly Gly Lys Val Thr Glu Leu Leu
            180                 185                 190
```

```
Thr Ser Ala Pro Pro Glu Leu Leu Lys Glu Ala Met Ser Gln Leu His
        195                 200                 205

Thr Ala Met Gly Glu Val Ala Asp Leu Gln Arg Ala Val Lys Ala Glu
        210                 215                 220

Val Ala Gly Glu Pro Ala Arg Ser Ala Thr Ala Ala Ala Val Ala
225                 230                 235                 240

Pro Leu Gln Ser Gly Glu Ser Glu Val Asn Val Glu Pro Ala Asp Lys
                245                 250                 255

Ala Leu Ala Glu Gly Leu Gln Glu Gln Phe Gly Leu Glu Ala Glu Gln
                260                 265                 270

Tyr Leu Gly Glu Gln Pro His Gly Thr Tyr Ser Asp Ala Glu Val Met
        275                 280                 285

Ala Leu Gly Leu Tyr Thr Asn Gly Glu Tyr Gln His Leu Asn Arg Ser
        290                 295                 300

Leu Arg Gln Glu Lys Gln Leu Asp Ala Gly Gln Ala Leu Ile Asp Gln
305                 310                 315                 320

Gly Met Ser Thr Ala Phe Glu Lys Ser Thr Pro Thr Glu Gln Leu Ile
                325                 330                 335

Lys Thr Phe Arg Gly Thr His Gly Gly Asp Ala Phe Asn Glu Val Ala
        340                 345                 350

Glu Gly Gln Val Gly His Asp Val Ala Tyr Leu Ser Thr Ser Arg Asp
        355                 360                 365

Pro Lys Val Ala Thr Asn Phe Gly Ser Gly Ser Ile Ser Thr Ile
        370                 375                 380

Phe Gly Arg Ser Gly Ile Asp Val Ser Asp Ile Ser Val Glu Gly Asp
385                 390                 395                 400

Glu Gln Glu Ile Leu Tyr Asn Lys Glu Thr Asp Met Arg Val Leu Leu
                405                 410                 415

Ser Ala Lys Asp Glu Arg Gly Val Thr Arg Arg Val Leu Glu Glu Ala
                420                 425                 430

Ser Leu Gly Glu Gln Ser Gly His Ser Lys Gly Leu Leu Asp Gly Leu
        435                 440                 445

Asp Leu Ala Arg Gly Ala Gly Gly Ala Asp Lys Pro Gln Glu Gln Asp
        450                 455                 460

Ile Arg Leu Lys Met Arg Gly Leu Asp Leu Ala
465                 470                 475

<210> SEQ ID NO 3
<211> LENGTH: 198
<212> TYPE: DNA
<213> ORGANISM: Aeromonas salmonicida

<400> SEQUENCE: 3
tgatggctcc agattgatga tggcgccatt agagcaggtc gccgccagcg gcactgttaa      60
tggtggctct cattttttag cttttcggtc agcaggatgg cgcgccgcgc tcagtacaaa     120
aatcgcgacc aatcccgata gtccctgttg atacccctctc ctagactggc ggcgaaacat     180
cacaagaaga caatcatc                                                    198

<210> SEQ ID NO 4
<211> LENGTH: 118
<212> TYPE: PRT
<213> ORGANISM: Aeromonas salmonicida

<400> SEQUENCE: 4

Met Asn Ser Leu Tyr His Ala Ala Ile His Gln Leu Phe Leu Ser Leu
```

```
1               5                  10                 15
Ser Leu Pro Gln Pro Gln Gln Glu Glu Ser Val Thr Ser Leu Gln Ile
            20                  25                 30

Gly Glu Leu Thr Cys His Leu Thr Glu His Pro Ala Asp Tyr Leu Leu
            35                  40                 45

Met Phe Thr Arg Leu Glu Val Ala Ser Gly Ala Gln Ala Ala Ala Gln
        50                  55                 60

Asn Leu Phe Ser Gln Asp Pro Cys Lys Pro Val Leu Gly Phe Asp Pro
65                  70                  75                 80

Asp Asp Leu Thr Pro Val Leu Trp Ser Arg Gln Pro Leu Gln Gln Leu
                85                  90                 95

Asp Arg Ala Gln Ile His His Gln Val Glu Gln Leu Val Ser Ala Ala
            100                 105                110

Asp Glu Leu Ser Arg Trp
            115

<210> SEQ ID NO 5
<211> LENGTH: 357
<212> TYPE: DNA
<213> ORGANISM: Aeromonas salmonicida

<400> SEQUENCE: 5
ttaccacctg cttagctcgt cagcggcaga gaccagttgc tccagctggt gatggatctg      60
ggcgcgatcc agctgctgca acggctggcg actccacaac accggcgtca gatcgtcggg     120
gtcaaaaccc agaacggggtt tgcaagggtc ctgactaaaa aggttttgcg cggcggcctg    180
ggcgccgcta gctacctcaa gacgggtaaa catcagcaga tagtcggctg ggtgctcggt    240
caggtggcag gtcagttcgc cgatctgcag gctggtgacg ctttcctcct gctgcggctg    300
aggaagcgag agggagagaa acagctggtg gatggcggcg tgataaagag agttcat      357
```